United States Patent

Ruscher et al.

[11] Patent Number: 5,560,793
[45] Date of Patent: Oct. 1, 1996

[54] APPARATUS AND METHOD FOR STRETCHING AN ELASTOMERIC MATERIAL IN A CROSS MACHINE DIRECTION

[75] Inventors: Edward H. Ruscher, Appleton; Robert E. Vogt, Neenah, both of Wis.

[73] Assignee: Kimberly-Clark Corporation, Neenah, Wis.

[21] Appl. No.: 510,940

[22] Filed: Aug. 3, 1995

Related U.S. Application Data

[63] Continuation of Ser. No. 213,751, Mar. 14, 1994, abandoned.

[51] Int. Cl.⁶ ........................................ B32B 31/16
[52] U.S. Cl. ..................... 156/73.1; 156/164; 156/229; 156/496; 156/580.1; 26/90; 264/290.2
[58] Field of Search ................................... 156/160, 163, 156/164, 229, 494, 495, 496, 73.1, 580.1; 26/88, 90, 91, 71, 72, 87; 425/66; 264/290.2

[56] References Cited

U.S. PATENT DOCUMENTS

| | | | |
|---|---|---|---|
| 3,644,157 | 2/1972 | Draper | 156/160 |
| 3,719,540 | 3/1973 | Hall | 156/267 |
| 3,807,004 | 4/1974 | Anderson | 26/88 |
| 3,833,973 | 9/1974 | Schwarz | 26/59 |
| 4,735,673 | 4/1988 | Piron | 156/496 |
| 4,925,520 | 5/1990 | Beaudoin et al. | 156/494 |
| 4,943,340 | 7/1990 | Ujimoto et al. | 156/496 |
| 5,000,806 | 3/1991 | Merkatoris et al. | 156/161 |
| 5,043,036 | 8/1991 | Swenson | 156/160 |
| 5,087,320 | 2/1992 | Neuwirth | 156/580.2 |
| 5,296,080 | 3/1994 | Merkatoris et al. | 156/496 |
| 5,308,345 | 5/1994 | Herrin | 604/385.2 |

FOREIGN PATENT DOCUMENTS

| | | |
|---|---|---|
| 571136 | 12/1961 | Belgium . |
| 0338662A2 | 10/1989 | European Pat. Off. . |
| 0379763A1 | 8/1990 | European Pat. Off. . |
| 0443244A1 | 8/1991 | European Pat. Off. . |
| 0449548A2 | 10/1991 | European Pat. Off. . |
| 1117811 | 12/1953 | France . |
| 3621205 | 1/1988 | Germany . |

OTHER PUBLICATIONS

Patent Abstracts of Japan, vol. 007 No. 203 (M–241), 8 Sep. 1983 & JP–A–58 102732 (Kobe Seikosho KK) 18 Jun. 1983, Abstract.

Primary Examiner—James Sells
Attorney, Agent, or Firm—Jeffrey B. Curtin

[57] ABSTRACT

An apparatus and method for stretching a continuously moving elastomeric web in a cross machine direction includes a pair of rotatable, cylindrical rims which are located adjacent the elastomeric web. A supporting mechanism is connected to the cylindrical rims to guide the rims for rotation about their axes. The axes of the cylindrical rims are oriented to position the rims at a close spacing at a first location and a far spacing at a second location. The far spacing is substantially greater than the close spacing relative to the elastic web path. A gripping means is located on the cylindrical rims such that, as the rims are rotated by a driving means, the gripping means receives the elastomeric web and holds the elastomeric web as it is stretched in the cross machine direction. The driving means is connected to the cylindrical rims. In addition, each cylindrical rim may have a center opening therethrough defined by its inner circumferential surface. A facing sheet may be supplied through the center opening and bonded to the stretched elastomeric web to provide a laminated web which is stretchable in the cross machine direction.

31 Claims, 4 Drawing Sheets

APPARATUS AND METHOD FOR STRETCHING AN ELASTOMERIC MATERIAL IN A CROSS MACHINE DIRECTION

This is a continuation of application Ser. No. 08/213,751 filed on Mar. 14, 1994, abandoned.

BACKGROUND OF THE INVENTION

1. Field of the Invention

The present invention relates to an apparatus and method for stretching a continuously moving elastomeric web in a cross machine direction. The invention particularly concerns an apparatus and method for stretching a continuously moving elastomeric material in a cross machine direction and bonding the material to at least one facing sheet thereby providing a stretch-bonded laminate material which is stretchable in the cross machine direction.

2. Description of the Related Art

Absorbent articles, such as disposable infant diapers, feminine care products, incontinence garments and the like, have included stretch-bonded laminate materials. For example, particular absorbent article designs have used stretch-bonded laminate materials for their leg and waist elastics.

Several different conventional methods exist for stretching elastomeric materials in the cross machine direction. Some conventional methods utilize a pair of canted wheels to stretch the elastomeric material in the cross machine direction. For example, U.S. Pat. No. 5,043,036 to Swenson describes an apparatus for stretching an elastomeric material in the cross machine direction which includes two circular pulleys which are canted about their axes. Other conventional methods for stretching elastomeric materials in the cross machine direction utilize a series of gripping devices which are arranged to successively grip and stretch the elastomeric material in the cross machine direction.

Conventional apparatus and methods for stretching an elastomeric material in the cross machine direction, such as those described above, have not been sufficiently satisfactory. For example, the devices may be overly complex and expensive and may not be capable of continuous operation at high speeds. The conventional devices also may not have the capability to provide the web paths which are necessary to laminate facing sheets to the stretched elastomeric web to provide stretch-bonded laminate materials. For example, the conventional devices may be useful in applying individual components, such as waist elastics, to an absorbent article but may not be useful in a laminating process. In addition, many of the conventional apparatus utilize mechanical gripping means or pins which may negatively affect the side edges of the stretched elastomeric material.

SUMMARY OF THE INVENTION

In response to the discussed difficulties and problems encountered in the prior art, a new apparatus and method for stretching an elastomeric material in a cross machine direction have been discovered.

In one aspect, the present invention can provide an apparatus for stretching a continuously moving elastomeric web in a cross machine direction. The apparatus includes a supplying means for continuously moving the elastomeric web in a machine direction along an elastomeric web path. A pair of rotatable, cylindrical rims are located adjacent the elastomeric web such that the elastomeric web moves between the cylindrical rims. Each of the cylindrical rims has an axis, an inner circumferential surface and an outer circumferential surface. A supporting means is connected to the cylindrical rims for guiding the rims for rotation about their axes. The axes are oriented to position the rims at a close spacing at a first location and a far spacing at a second location. The far spacing is greater than the close spacing relative to the elastomeric web path. A gripping means is located on the cylindrical rims for receiving the elastomeric web and holding the web as it is stretched. A driving means is connected to the cylindrical rims and is used to rotate the rims. As the cylindrical rims are rotated by the driving means, the elastomeric web is received by the gripping means at the close spacing at the first location and transported to the far spacing at the second location thereby stretching the elastomeric web in the cross machine direction. In particular, the supporting means may include at least three support rollers which are rotatably connected to the inner circumferential surface of the cylindrical rims. In addition, the driving means may include a pair of drive gears which are configured to engage and rotate a pair of ring gears which are connected to the inner circumferential surface of the cylindrical rims. In use, the drive gears engage and rotate the ring gears thereby rotating the cylindrical rims.

In another aspect, the present invention can provide a method for stretching a continuously moving elastomeric web in a cross machine direction. An elastomeric web is moved along an elastomeric web path in a machine direction. A pair of rotatable, cylindrical rims are provided adjacent the elastomeric web. Each of the cylindrical rims has an axis, an inner circumferential surface, and an outer circumferential surface. The cylindrical rims are guided for rotation about their axes by a supporting means which is connected to the cylindrical rims. The axes of the rims are oriented to position the rims at a close spacing at a first location and a far spacing at a second location. The far spacing is substantially greater than the close spacing relative to the elastomeric web path. The elastomeric web is held between the first location and the second location by a gripping means as the cylindrical rims are rotated. Thus, the elastomeric web is transported from the close spacing at the first location to the far spacing at the second location thereby stretching the elastomeric web in the cross machine direction. The cylindrical rims are rotated by a driving means which is connected to the rims. The elastomeric web may also be elongated in the machine direction before it is stretched in the cross machine direction.

A further aspect of the present invention can provide a method for providing a laminated web which is stretchable in a cross machine direction. An elastomeric web is moved along an elastomeric web path in a machine direction. At least one facing sheet is moved along a facing sheet path. The elastomeric web is stretched in the cross machine direction thereby providing a stretched elastomeric web. The stretched elastomeric web and the facing sheet are positioned in a facing relationship and bonded together to provide the laminated web which is stretchable in the cross machine direction. The elastomeric web is stretched in the cross machine direction by a pair of rotatable cylindrical rims which are positioned adjacent the elastomeric web. Each of the cylindrical rims has an axis, an inner circumferential surface, and an outer circumferential surface. The cylindrical rims are guided for rotation about their axes by a supporting means which is connected to the rims. The axes of the cylindrical rims are oriented to position the rims at a close spacing at a first location and a far spacing at a second location. The far spacing is greater than the close spacing relative to the elastomeric web path. The elastomeric web is gripped between the first location and second location by a gripping means as the cylindrical rims are rotated. Thus, the elastomeric web is transported from the close spacing at the first location to the far spacing at the second location thereby stretching the elastomeric web in the cross machine direction. The cylindrical rims are rotated by a driving means which is connected to the rims. In particular, each cylindrical rim has a center opening therethrough defined by the inner circumferential surface of the rim. The facing sheet extends along the facing sheet path through the center opening of at least one of the cylindrical rims before being bonded to the stretched elastomeric web. The elastomeric web may also be elongated in a machine direction before it is bonded to the facing sheet, thereby providing a laminated web which is stretchable in both the machine direction and the cross machine direction.

The present invention, in its various aspects, can advantageously provide an apparatus and method which, when compared to conventional devices, can more efficiently provide a continuously moving elastomeric material which is stretched in a cross machine direction. The present invention can also provide less complicated web paths such that a facing sheet can be easily laminated to the continuously moving stretched elastomeric web to provide a laminated web which is stretchable in the cross machine direction and which can be used in the production of absorbent articles.

BRIEF DESCRIPTION OF THE DRAWINGS

The present invention will be more fully understood and further advantages will become apparent when reference is made to the following detailed description of the invention and the accompanying drawings. The drawings are merely representative and are not intended to limit the scope of the appended claims.

DETAILED DESCRIPTION OF THE INVENTION

The present invention provides an apparatus and method for stretching an elastomeric material in a cross machine direction. The apparatus and method are particularly useful for stretching a continuously moving elastomeric web in the cross machine direction, laminating it to a facing sheet and subsequently using it as a component in an absorbent article such as, for example, a disposable diaper. In particular, the stretched elastomeric material of the present invention can be used to provide stretchable outer ears on a disposable diaper to enhance the fit of the diaper about the waist of the wearer. The stretched elastomeric material may also provide the waist or leg elastics in a disposable diaper. In addition, it should be readily understood that the stretched elastomeric material of the present invention may be used in other types of absorbent articles, such as, for example, training pants, feminine care products, incontinence garments and the like. All of such alternative configurations are contemplated as being within the scope of the present invention.

As used herein, the terms "elastomeric" or "elastic" refer to any material that, upon application of a biasing force, is capable of being elongated or stretched in a specified direction from at least about 20 percent to about 400 percent and which will recover to within at least from about 5 to about 35 percent of its original length after being elongated or stretched.

As used herein, the term "cross machine direction" refers to a direction that is substantially perpendicular to a machine direction along which the elastomeric web of the present invention travels.

Figure 1:
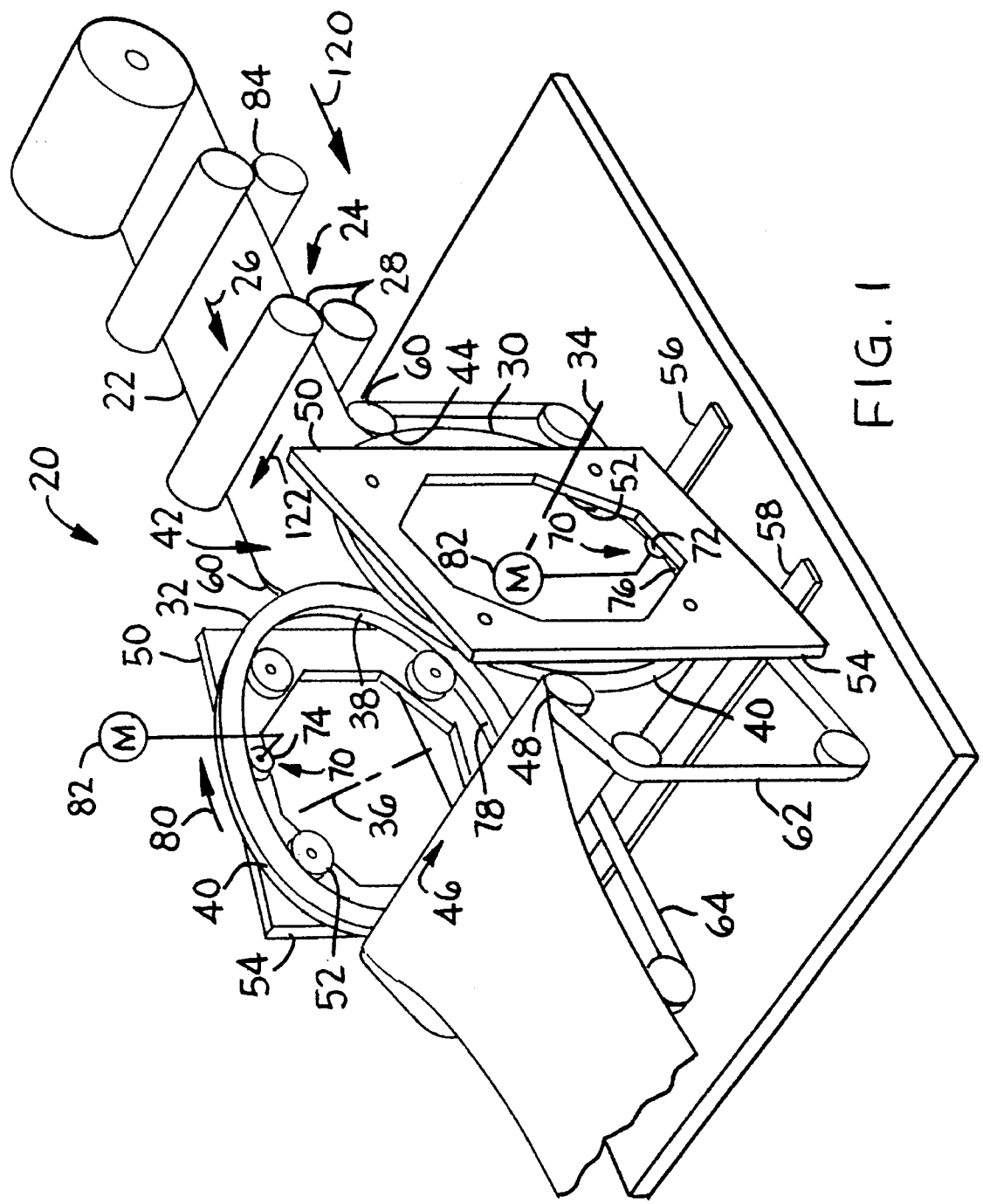
FIG. 1 representatively shows a perspective view of one example of an apparatus of the present invention.
Figure 2:
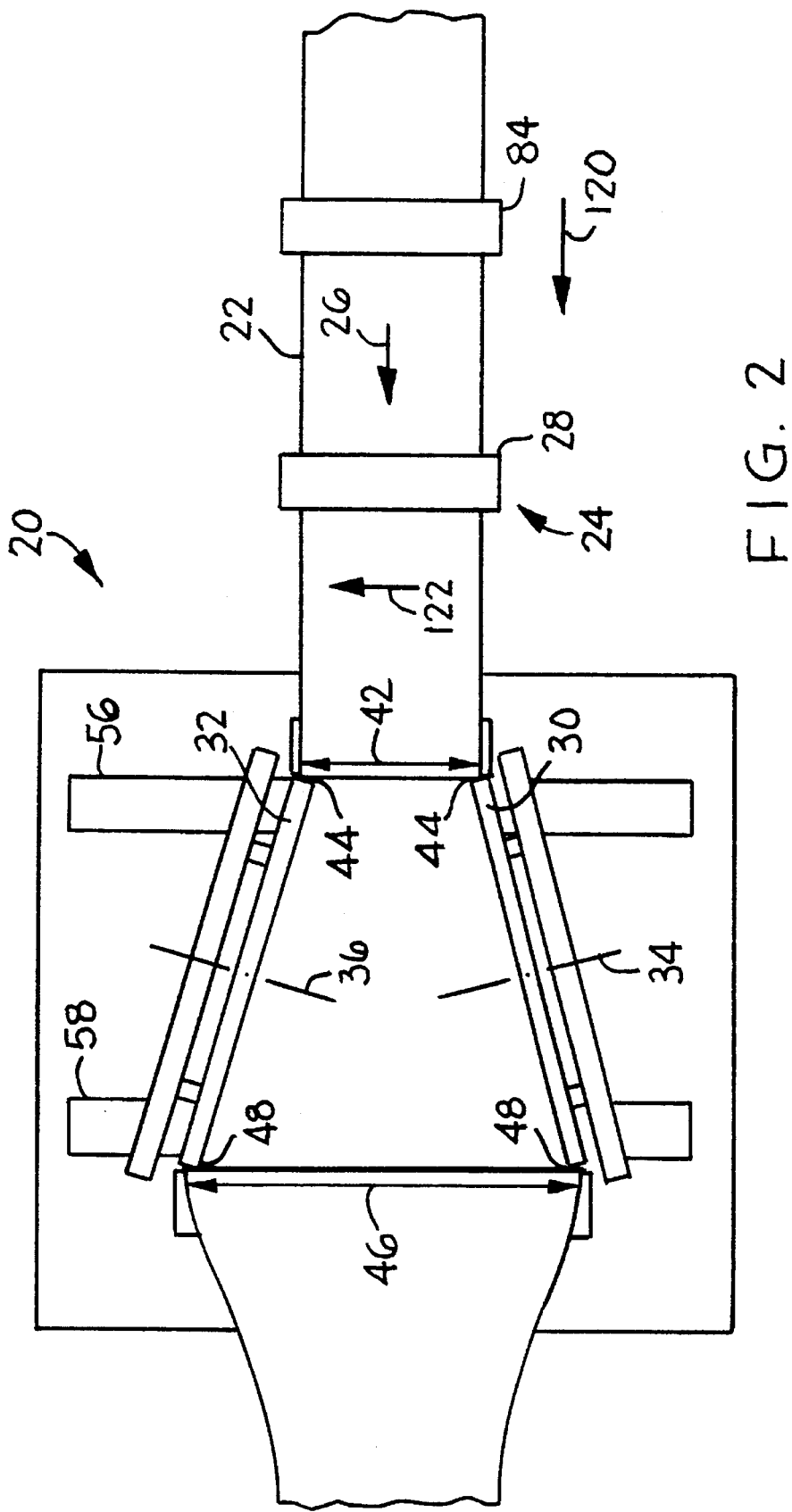
FIG. 2 representatively shows a top plan view of the apparatus of FIG. 1.

An apparatus and method for stretching a continuously moving elastomeric web in a cross machine direction are representatively illustrated in FIGS. 1 and 2. The apparatus, which is generally indicated at 20, and method include a supplying means 24 for continuously moving an elastomeric web 22 in a machine direction 120 along an elastomeric web path 26. A pair of rotatable, cylindrical rims 30 and 32 are located adjacent the side edges of the elastomeric web 22. Each of the rims has an axis 34 and 36, an inner circumferential surface 38, and an outer circumferential surface 40. A supporting means 50 is connected to the cylindrical rims 30 and 32 to guide the rims for rotation about their axes 34 and 36. As representatively illustrated in FIG. 2, the axes 34 and 36 are oriented in a position such that the rims 30 and 32 are at a close spacing 42 at a first location 44 and a far spacing 46 at a second location 48. The far spacing 46 is substantially greater than the close spacing 42 relative to the elastomeric web path 26. The apparatus 20 and method, as representatively illustrated in FIGS. 1 and 2, further include a gripping means 60 which is located on the cylindrical rims 30 and 32 for receiving and holding the elastomeric web 22 as it is stretched. A driving means 70 is connected to the cylindrical rims 30 and 32 to rotate the rims. In use, as the cylindrical rims 30 and 32 are rotated by the driving means 70, the elastomeric web 22 is received by the gripping means 60 at the close spacing 42 at the first location 44 and transported to the far spacing 46 at the second location 48 thereby stretching the elastomeric web 22 in the cross machine direction 122.

As representatively illustrated in FIG. 1, the supplying means 24 is configured to continuously move an elastomeric web 22 in the machine direction 120 along an elastomeric web path 26. For example, the supplying means 24 may include a pair of rotatable nip rollers 28 which are configured to move the elastomeric web 22 at the desired rate of speed. The pair of rotatable nip rollers 28 may be driven by any means known to those skilled in the art. For example, the rotatable nip rollers 28 may be connected to a primary lineshaft of the apparatus 20 by suitable gearing or, in the alternative, the rotatable nip rollers 28 may be separately driven by an electric motor. The supplying means 24 can be configured to continuously move the elastomeric web 22 at any rate of speed depending upon the desired final use and configuration of the elastomeric web 22. For example, the supplying means 24 may continuously move the elastomeric web 22 at a speed of from about 0.3 to about 20 feet per second (0.1 to about 6 meters per second).

Each rotatable, cylindrical rim 30 and 32, as representatively illustrated in FIGS. 1 and 2, has an axis 34 and 36, respectively, an inner circumferential surface 38 and an outer circumferential surface 40. Each cylindrical rim 30 and 32 further has a center opening therethrough which is defined by the inner circumferential surface 38. The diameter of the inner circumferential surface 38 and the outer circumferential surface 40 of the cylindrical rims 30 and 32 will vary depending upon the width of the elastomeric web 22 and the desired amount of stretch in the cross machine direction 122. For example, the inner circumferential surface 38 may have a diameter of from about 24 to about 150 inches (61 to about 381 centimeters), desirably from about 48 to about 60 inches (122 to about 152 centimeters) and the outer circumferential surface 40 may have a diameter of from about 28 to about 160 inches (71 to about 406 centimeters), desirably from about 53 to about 66 inches (135 to about 168 centimeters). Thus, the corresponding size of the center opening in the cylindrical rims 30 and 32 can also vary. The cylindrical rims 30 and 32 are located adjacent the side edges of the elastomeric web 22. The cylindrical rims 30 and 32 may be made from any material well known to those skilled in the art. For example, the cylindrical rims may be made from steel, aluminum or a plastic material.

The illustrated example of the supporting means 50 includes at least three support rollers 52 which are rotatably connected to a pair of support frames 54. The support rollers 52 are also rotatably connected to the inner circumferential surface 38 of the cylindrical rims 30 and 32. The support rollers 52 and support frames 54 are configured to guide the cylindrical rims 30 and 32 for rotation about their respective axis, 34 and 36. It is desirable that the support frames 54, as representatively illustrated in FIG. 1, have frame openings therethrough which are in alignment with the center openings defined by the inner circumferential surface 38 of the cylindrical rims 30 and 32.

The support rollers 52 and support frames 54 are located such that the axes 34 and 36 of the cylindrical rims 30 and 32, respectively, are oriented to position the rims 30 and 32 at a close spacing 42 at a first location 44 and a far spacing 46 at a second location 48, as representatively illustrated in FIG. 2. The far spacing 46 is substantially greater than the close spacing 42 relative to the elastomeric web path 26. Desirably, the far spacing 46 is from about 20 percent to about 400 percent greater than the close spacing 42 and, more desirably, the far spacing 46 is from about 150 percent to about 300 percent greater than the close spacing 42. Thus, the cylindrical rims 30 and 32 are canted or angled outwards relative to the elastomeric web path 26 as one travels in the machine direction 120 from the first location 44 to the second location 48.

Desirably, the support rollers 52 and the inner circumferential surface 38 of the cylindrical rims 30 and 32, as representatively illustrated in FIG. 1, are configured in a mating relationship such that the alignment of the cylindrical rims 30 and 32 is maintained as the rims are rotated. For example, the support rollers 52 may include a groove therein which is configured to receive the inner circumferential surface 38 of the cylindrical rims 30 and 32. Desirably, the support rollers 52 are V-grooved Load Runners manufactured by Osborne Mfg. Co. located in Cleveland, Ohio.

The supporting means 50, as representatively illustrated in FIGS. 1 and 2, may further include an adjusting means 56 for changing the position and orientation of the support frames 54 to vary the close spacing 42 and far spacing 46 between the cylindrical rims 30 and 32. Thus, the position of the support frames 54 and the corresponding orientation of the axes 34 and 36 of the cylindrical rims 30 and 32, respectively, may be varied such that the close spacing 42 at the first location 44 and the far spacing 46 at the second location 48 are also varied. The adjusting means 56, as representatively illustrated in FIGS. 1 and 2, may include a pair of carrier slides 58 which are slidably connected to the supporting means 50 and support frames 54 such that the position and orientation of the cylindrical rims 30 and 32 can be varied as desired. The carrier slides 58 may include any device known to those skilled in the art. For example, the carrier slides 58 may be dovetail slides manufactured by Milwaukee Slide Co. which is located in Milwaukee, Wis. By varying the orientation and spacing of the cylindrical rims 30 and 32, the amount of stretch in the elastomeric web in the cross machine direction 122 can be varied as desired.

The illustrated example of the gripping means 60 includes a pair of endless belts 62 and 64 which are configured to receive the elastomeric web 22 and hold the elastomeric web 22 against the outer circumferential surface 40 of the cylindrical rims 30 and 32. As representatively illustrated in FIGS. 1 and 2, each endless belt 62 and 64 is provided for movement along a predetermined path such that the belts 62 and 64 receive the elastomeric web 22 at the first location 44 and hold the elastomeric web 22 against the outer circumferential surface 40 of the cylindrical rims 30 and 32 as the rims are rotated to the second location 48. The endless belts 62 and 64 may be maintained along the predetermined path by any means known to those skilled in the art such as, for example, a series of idler pulleys. The outer circumferential surface 40 of the cylindrical rims 30 and 32 may further include a groove therein for receiving the belts 62 and 64 to ensure proper alignment of the belts 62 and 64 about the outer circumferential surface 40. Endless belts which are suitable for use with the present invention are well known to those skilled in the art. For example, the endless belts 62 and 64 may be polyurethane timing belts manufactured by Brecoflex which is located in Eatontown, N.J.

In use, the elastomeric web 22 is received between the endless belts 62 and 64 and the outer circumferential surface 40 of the cylindrical rims 30 and 32 at the first location 44. As the cylindrical rims 30 and 32 are rotated in the direction indicated by the arrow 80 associated therewith, the endless belts 62 and 64 hold the elastomeric web 22 against the outer circumferential surface 40 of the cylindrical rims 30 and 32 between the first location 44 and the second location 48. Thus, the endless belts 62 and 64 hold the elastomeric web 22 as it is moved in the machine direction 120 from the close spacing 42 at the first location 44 to the far spacing 46 at the second location 48 thereby stretching the elastomeric web in the cross machine direction 122.

As representatively illustrated in FIGS. 1 and 2, the driving means 70 may include a pair of drive gears 72 and 74 which are configured to engage and rotate a pair of ring gears 76 and 78. The ring gears 76 and 78 are connected to the inner circumferential surface 38 of the cylindrical rims 30 and 32, respectively. The ring gears 76 and 78 are connected to the inner circumferential surface 38 of the cylindrical rims 30 and 32 by any means known to those skilled in the art. For example, the ring gears 76 and 78 may be bolted, screwed, or welded to the cylindrical rims 30 and 32.

The drive gears 72 and 74 may be rotated by any means known to those skilled in the art. For example, each drive gear 72 and 74 may be rotated by an electric motor 82. The drive gears 72 and 74 may be driven separately or may be connected together by a single shaft which is driven. Thus, in use, the electric motor 82 rotates the drive gears 72 and 74 which engage and rotate the ring gears 76 and 78, respectively, thereby rotating the cylindrical rims 30 and 32 in the direction indicated by the arrow 80 associated therewith. As the cylindrical rims 30 and 32 are rotated, the elastomeric web 22 is received by the gripping means 60 at the close spacing 42 at the first location 44 and transported to the far spacing 46 at the second location 48 thereby stretching the elastomeric web 22 in the cross machine direction 122.

In an alternative aspect of the invention, the driving means 70 may be provided by the endless belts 62 and 64 which are configured to receive the elastomeric web 22 and hold the elastomeric web 22 against the outer circumferential surface 40 of the cylindrical rims 30 and 32. As representatively illustrated in FIGS. 1 and 2, the endless belts 62 and 64 are configured in a predetermined path around a series of idler pulleys such that they engage a portion of the outer circumferential surface 40 of the cylindrical rims 30 and 32 between the first location 44 and the second location 48. The endless belts 62 and 64 may be driven by any means known to those skilled in the art. For example, an idler roller may be driven by an electric motor causing the endless belts 62 and 64 to move thereby rotating the cylindrical rims 30 and 32 in the direction indicated by the arrow 80 associated therewith. Thus, in this alternative aspect of the invention, the endless belts 62 and 64 may provide the gripping means 60 and the driving means 70.

The apparatus and method of the present invention, as representatively illustrated in FIGS. 1 and 2, may further include a stretching means for elongating the elastomeric web 22 in the machine direction 120 before the elastomeric web 22 is stretched in the cross machine direction 122. For example, the apparatus 20 of the invention may further include a second set of rotatable nip rollers 84 located upstream from the first set of rotatable nip rollers 28. In use, each set of nip rollers 28 and 84 may be driven at a variable speed to elongate the elastomeric web 22 in the machine direction 120 before it is moved to the cylindrical rims 30 and 32. The second set of nip rollers 84 may be driven by any means known to those skilled in the art such as, for example, an electric motor.

It will be further appreciated that the apparatus and method of the invention, as representatively illustrated in FIGS. 1 and 2, can utilize one, or in the alternative, two, three, or more pairs of cylindrical rims in series to achieve the desired stretch in the cross machine direction.

In another aspect, the present invention concerns an apparatus and method for providing a laminated web which is stretchable in a cross machine direction. As representatively illustrated in FIG. 3, an elastomeric web 22 is moved in a machine direction 120 along an elastic web path 26 and at least one facing sheet 102 is moved along a facing sheet path 104. The elastomeric web 22 is stretched in the cross machine direction 122 to provide a stretched elastomeric web. The stretched elastomeric web is positioned in a facing relationship with the facing sheet 102 and bonded to the facing sheet 102 to provide a laminated web 100 which is stretchable in the cross machine direction 122.

Before the elastomeric web 22 is bonded to the facing sheet 102, the elastomeric web 22 is stretched in the cross machine direction 122 by an apparatus and method such as is representatively illustrated in FIGS. 1 and 2. As illustrated, an apparatus, generally indicated at 20, is used to stretch the elastomeric web 22 in the cross machine direction 122. The apparatus 20 includes a pair of rotatable cylindrical rims 30 and 32 which are located adjacent the side edges of the elastomeric web 22. Each of the cylindrical rims 30 and 32 has an axis 34 and 36, an inner circumferential surface 38 and an outer circumferential surface 40. The cylindrical rims 30 and 32 are guided by a supporting means 50 for rotation about their axes 34 and 36. As representatively illustrated in FIG. 2, the axes 34 and 36 of the cylindrical rims 30 and 32 are oriented to position the rims 30 and 32 at a close spacing 42 at a first location 44 and a far spacing 46 at a second location 48. The far spacing 46 is substantially greater than the close spacing 42 relative to the elastomeric web path 26. As the cylindrical rims 30 and 32 are rotated in the direction indicated by the arrow 80 associated therewith, the elastomeric web 22 is gripped and transported between the close spacing 42 at the first location 44 and the far spacing 46 at the second location 48 to stretch the elastomeric web 22 in the cross machine direction 122. The cylindrical rims 30 and 32 are rotated by a driving means 70 which is connected to the rims 30 and 32.

Figure 3:
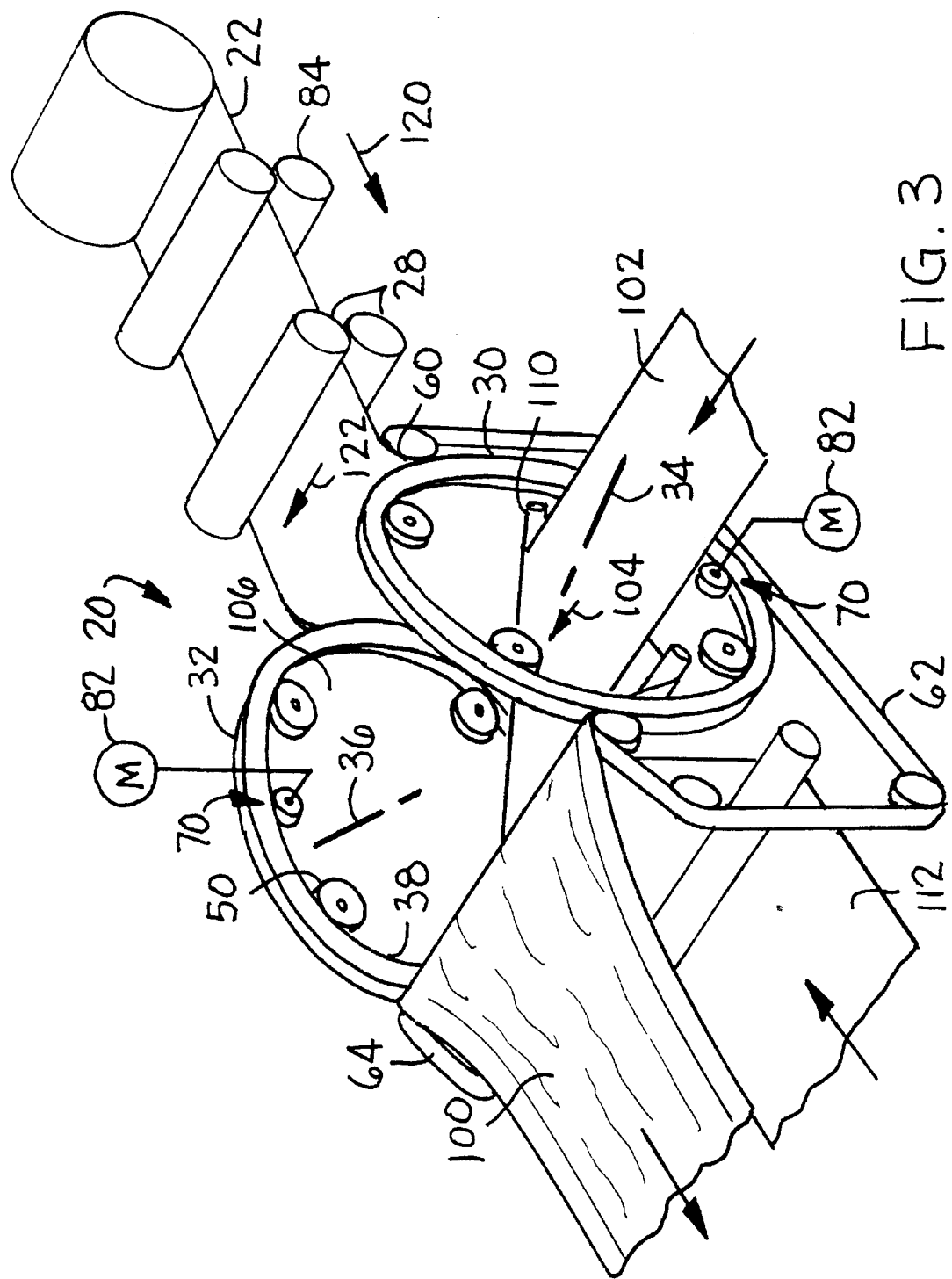
FIG. 3 representatively shows a perspective view of another example of an apparatus of the present invention.

As representatively illustrated in FIG. 3, each cylindrical rim 30 and 32 has a center opening 106 therethrough which is defined by the inner circumferential surface 38 of the cylindrical rims 30 and 32. The diameter of the inner circumferential surface 38 is great enough to allow the facing sheet 102 to extend through at least one of the cylindrical rims 30 and 32 before it is bonded to the stretched elastomeric web. In this configuration, it is desirable that the support frames 54, as representatively illustrated in FIG. 1, have frame openings therethrough which are in alignment with the center openings 106 of each cylindrical rim 30 and 32 to allow the facing sheet 102 to extend through both the support frames 54 and the cylindrical rims 30 and 32. The size of the frame opening will vary depending on the size of the center opening 106 and the corresponding diameter of the inner circumferential surface 38 of the cylindrical rims 30 and 32. Desirably, the frame opening has a width and heigth of from about 20 to about 140 inches (51 to about 356 centimeters), desirably from about 40 to about 52 inches (102 to about 132 centimeters) which corresponds to the diameter of the inner circumferential surface 38. Thus, the present invention provides less complicated paths to supply materials which can be laminated to the stretched elastomeric web because the cylindrical rims 30 and 32 are not supported and driven about a hub or shaft along their axes 34 and 36.

A web guiding means 110 may be positioned along the facing sheet path 104 and between the cylindrical rims 30 and 32 to properly orient the facing sheet 102 along the machine direction 120 before the facing sheet 102 is bonded to the stretched elastomeric web. Web guiding means are well known to those skilled in the art. For example, as representatively illustrated in FIG. 3, the web guiding means 110 may include a shaft positioned at a forty-five degree angle to change the orientation of the facing sheet 102.

The elastomeric web 22, as representatively illustrated in FIG. 3, may be bonded to the facing sheet 102 by any method known to those skilled in the art. For example, the elastomeric web 22 may be stretched in the cross machine direction 122 and bonded to the facing sheet 102 thermally, ultrasonically or adhesively. In addition, a second facing sheet 112 may be bonded to the stretched elastomeric web such that the stretched elastomeric web is positioned between two facing sheets. Thus, the elastomeric web 22 is stretched in the cross machine direction and bonded to at least one facing sheet 102. Upon relaxing the materials, the elastomeric web 22 gathers the facing sheet 102 thereby providing a laminated web 100 which is stretchable in the cross machine direction 122 to the extent that the facing sheet 102 allows the elastomeric web 22 to stretch. In an alternative aspect of the invention, the elastomeric web 22 may be elongated in the machine direction 120 before it is stretched in the cross machine direction 122 and bonded to the facing sheet 102. Thus, the laminated web 100 may be stretchable in both the machine direction and the cross machine direction to the extent that the facing sheet 102 allows the elastomeric web to stretch.

The facing sheet 102 may be provided by any material known to those skilled in the art. For example, the facing sheet 102 may include a nonwoven material such as a spunbond, meltblown, spun laced or carded polymeric material, a film material such as a polyolefin or polyurethane film, a foam material or combinations thereof. The facing sheet 102 may be elastic or nonelastic. In a specific aspect, the facing sheet 102 is formed from a nonwoven material such as a spunbond or meltblown polyethylene or polypropylene material having a basis weight of from about 5 to about 50 grams per square meter.

The laminated web of the different aspects of the present invention provides a material which, when stretched in the cross machine direction, substantially maintains its length in the machine direction with minimal necking. In addition, the amount of force required to stretch the laminated web of the present invention in the first cycle is substantially the same as the amount of force required in subsequent cycles.

The different aspects of the invention can advantageously provide an elastomeric web which has been stretched in the cross machine direction. The stretched elastomeric web may also be laminated to at least one facing sheet to provide a laminated web which is stretchable in the cross machine direction. The elastomeric web may be made of any suitable material having elastic or stretchable properties. Examples of such materials include films or layers of natural rubber, synthetic rubber, or thermoplastic elastomeric polymers. Furthermore, the elastomeric web may be a nonwoven material such as, for example, a spunbond, meltblown or carded web. The elastomeric web may be a uniform layer or sheet or it may include a web having a center elastic material with strips of elastic or nonelastic material bonded to the side edges thereof. In such a configuration, the elastic or nonelastic strips of material may or may not be included in the final product. In a specific aspect, the elastomeric web may be an elastic material such as a 1.2 mil polyurethane film made by Deerfield Urethane using B. F. Goodrich #58661 resin.

The different aspects of the invention may be configured such that the elastomeric web is stretched in the cross machine direction in an amount of from about 20 to about 400 percent. Desirably, the elastomeric web is stretched in the cross machine direction in an amount of from about 150 to about 300 percent and, more desirably, the elastomeric web is stretched in the cross machine direction in an amount of from about 200 to about 250 percent. The elastomeric web of the present invention may also be elongated in the machine direction in an amount of from about 20 to about 400 percent before it is stretched in the cross machine direction.

Thus, the different aspects of the invention can more efficiently provide an elastomeric material which is stretched in the cross machine direction. The present invention also allows for less complicated web paths compared to conventional methods for providing stretch-bonded laminate materials because the cylindrical rims are not driven and supported about a hub or shaft along their axes.

Figure 4:
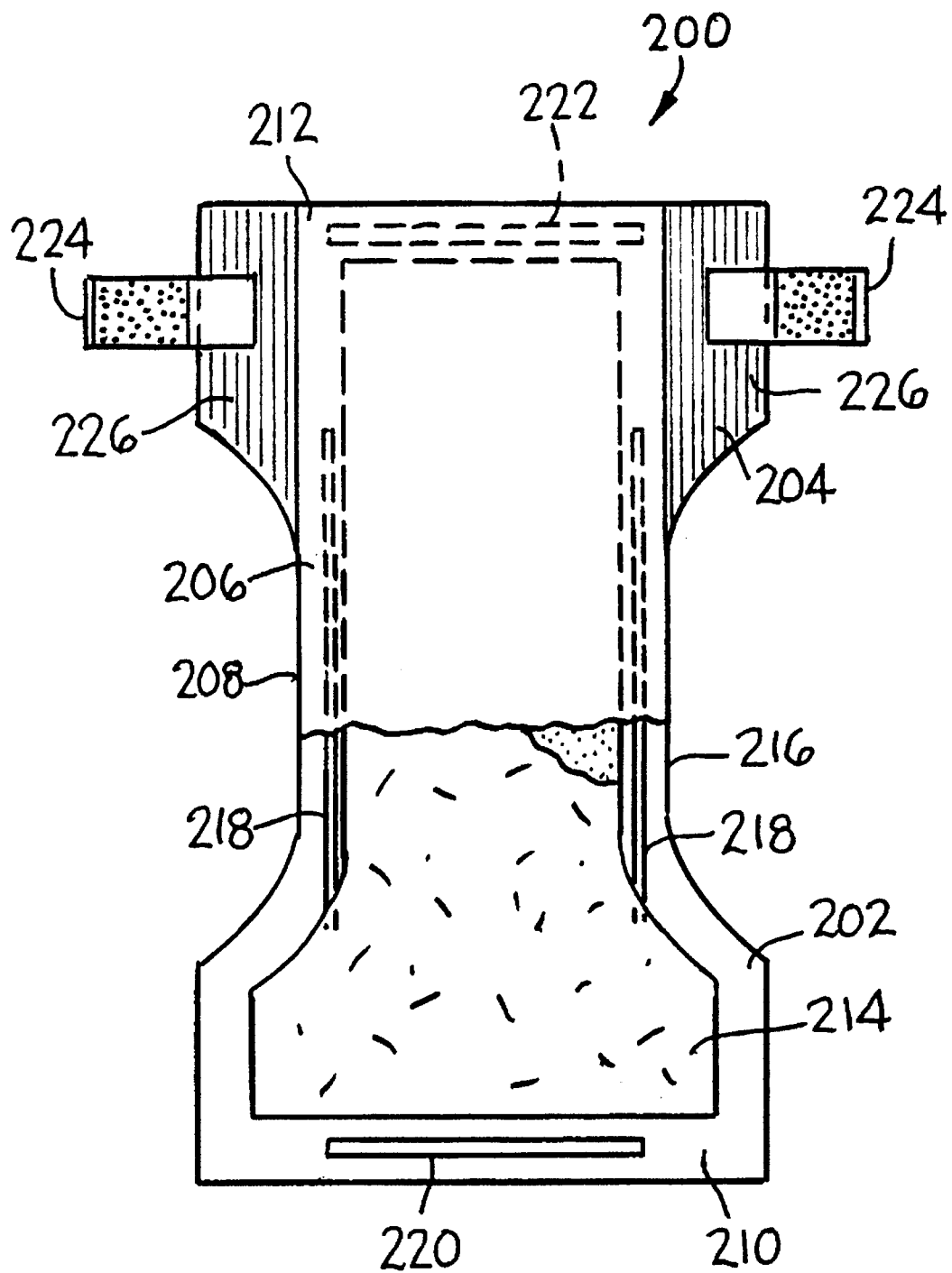
FIG. 4 representatively shows an absorbent article utilizing the stretched elastomeric web produced by the apparatus and method of the present invention.

The stretched elastomeric web of the different aspects of the present invention may be used in an absorbent article, such as a disposable diaper which is representatively illustrated in FIG. 4. The absorbent article 200 defines a front portion 202, a rear portion 204, and a crotch portion 206 connecting the front portion 202 and the rear portion 204.

The absorbent article 200 includes a bodyside liner 210, an outer cover 212, and an absorbent core 214 located between the bodyside liner 210 and the outer cover 212. As used herein, reference to a front portion refers to that part of the absorbent article which is generally located on the front of a wearer when in use. Reference to the rear portion refers to the portion of the article generally located at the rear of the wearer when in use, and reference to the crotch portion refers to that portion which is generally located between the legs of the wearer when in use.

The crotch portion 206 has opposite longitudinal side portions 208 which include a pair of elasticized, longitudinally extending leg cuffs 216. The leg cuffs 216 are generally adapted to fit about the legs of a wearer when in use and serve as a mechanical barrier to the lateral flow of body exudates. The leg cuffs 216 are elasticized by a pair of leg elastics 218. The absorbent article 200 further includes a front waist elastic 220 and a rear waist elastic 222. The rear portion 204 of the absorbent article 200 may further include a pair of stretchable ears 226 attached thereto. A fastening means 224 such as snap closures, hook and loop fasteners, mushroom fasteners or tape fasteners may be attached to the stretchable ears 226. The fastening means 224 is intended to hold the absorbent article 200 about the waist of the wearer when in use.

The bodyside liner 210 of the absorbent article 200, as representatively illustrated in FIG. 4, suitably presents a body facing surface which is compliant, soft feeling, and non-irritating to the Wearer's skin. Further, the bodyside liner 210 may be less hydrophilic than the absorbent core 214, to present a relatively dry surface to the wearer, and may be sufficiently porous to be liquid permeable, permitting liquid to readily penetrate through its thickness. A suitable bodyside liner 210 may be manufactured from a wide selection of web materials such as porous foams, reticulated foams, apertured plastic films, natural fibers (for example, wood or cotton fibers), synthetic fibers (for example, polyester or polypropylene fibers), or a combination of natural and synthetic fibers. The bodyside liner 210 is suitably employed to help isolate the wearer's skin from liquid held in the absorbent core.

Various woven and nonwoven fabrics can be used for the bodyside liner 210. For example, the bodyside liner may be composed of a meltblown or spunbonded web of polyolefin fibers. The bodyside liner 210 may also be a bonded carded web composed of natural and/or synthetic fibers. The bodyside liner 210 may be composed of a substantially hydrophobic material, and the hydrophobic material may, optionally, be treated with a surfactant or otherwise processed to impart a desired level of wettability and hydrophilicity. In a particular aspect of the present invention, the bodyside liner 210 comprises a nonwoven, spunbond, polypropylene fabric composed of about 2.8–3.2 denier fibers formed into a web having a basis weight of about 22 grams per square meter and a density of about 0.06 grams per cubic centimeter. The fabric is surface treated with about 0.28 weight percent of a surfactant commercially available from Rohm and Haas Company under the trade designation Triton X-102.

The outer cover 212 of the absorbent article 200, as representatively illustrated in FIG. 4, may suitably be composed of a material which is either liquid permeable or liquid impermeable. It is generally preferred that the outer cover 212 be formed from a material which is substantially impermeable to liquids. For example, a typical outer cover can be manufactured from a thin plastic film or other flexible liquid impermeable material. For example, the outer cover 212 may be formed from a polyethylene film having a thickness of from about 0.012 millimeter (0.5 mil) to about 0.051 millimeter (2.0 mils). If it is desired to present the outer cover 212 with a more clothlike feeling, the outer cover 212 may comprise a polyethylene film having a nonwoven web laminated to the outer surface thereof, such as a spunbond web of polyolefin fibers. For example, a polyethylene film having a thickness of about 0.015 millimeter (0.6 mil) may have thermally laminated thereto a spunbond web of polyolefin fibers, which fibers have a thickness of about 1.5 to 2.5 denier per filament, which nonwoven web has a basis weight of about 24 grams per square meter (0.7 ounces per square yard). Methods of forming such clothlike outer covers are well known to those skilled in the art.

Further, the outer cover 212 may be formed of a woven or nonwoven fibrous web layer which has been totally or partially constructed or treated to impart a desired level of liquid impermeability to selected regions that are adjacent or proximate the absorbent core 214. Still further, the outer cover 212 may optionally be composed of a microporous "breathable" material which permits vapors to escape from the absorbent core 214 while still preventing liquid exudates from passing into the outer cover 212.

The absorbent core 214 of the absorbent article 200, as representatively illustrated in FIG. 4, may suitably comprise a fibrous web which includes a high absorbency material. As a general rule, the high absorbency material is present in the absorbent core 214 in an amount of from about 5 to about 100 weight percent based on total weight of the absorbent core to provide more effective performance. The absorbent core 214 may have any of a number of shapes. For example, the absorbent core 214 may be rectangular, I-shaped or T-shaped. It is generally preferred that the absorbent core 214 be narrower in the crotch portion 206 of the absorbent article 200 than in the front or rear portion, 202 or 204, respectively.

The outer cover 212 and bodyside liner 210 are generally adhered to one another so as to form a pocket in which the absorbent core 214 is located. Thus, the leg cuffs 216 are suitably formed by portions of the outer cover 212, and/or bodyside liner 210, which extend beyond the longitudinal sides of the absorbent core 214. Naturally, the leg cuffs 216 can also be formed from separate materials which are attached to the outer cover 212 and/or bodyside liner 210.

The leg cuffs 216, as representatively illustrated in FIG. 4, include leg elastics 218. Materials suitable for use in forming leg cuffs 216 and leg elastics 218 are known to those skilled in the art. For example, the stretched elastomeric web of the different aspects of the present invention may be utilized to provide the leg cuffs 216 or leg elastics 218. Similarly, the waist elastics 220 and 222 are well known to those skilled in the art and may include the stretched elastomeric web of the present invention.

The stretched elastomeric web of the present invention may also be utilized to form the stretchable ears 226 which are fastened to the rear portion 204 of the absorbent article 200. The fastening means 224 may be attached to the stretchable ears 226. The combination of the stretchable ears 226 and the fastening means 224 provide a better fit of the absorbent article about the waist of a wearer.

A wide variety of diaper configurations, as well as training pants, incontinence garments, and like configurations, are suitable for using the stretched elastomeric web of the present invention. Suitable diapers are described in greater detail in commonly assigned U.S. Patent application Ser. No. 07/757,760 entitled "Thin Absorbent Article Having Rapid Uptake Of Fluid" filed Sep. 11, 1991, now abandoned in the name of Hanson et al.

While the invention has been described in detail with respect to specific aspects thereof, it will be appreciated that those skilled in the art, upon attaining an understanding of the foregoing, may readily conceive of alterations to, variations of, and equivalents to these aspects. Accordingly, the scope of the present invention should be assessed as that of the appended claims and any equivalents thereto.

What is claimed is:

1. A method for stretching a continuously moving elastomeric web in a cross machine direction, said method comprising the steps of:
   a) moving said elastomeric web in a machine direction along an elastomeric web path;
   b) providing a pair of rotatable, cylindrical rims adjacent said elastomeric web wherein each of said rims has an axis, an inner circumferential surface, an outer circumferential surface and a center opening therethrough which allows access through said cylindrical rim when in use;
   c) guiding said cylindrical rims for rotation about said axes wherein said axes are oriented to position said rims at a close spacing at a first location and a far spacing at a second location, said far spacing being substantially greater than said close spacing relative to said elastomeric web path and wherein said guiding is provided by a supporting means which is connected to said inner circumferential surface of said cylindrical rims;
   d) holding said elastomeric web between said first location and said second location wherein said holding is provided by a gripping means which is located on said cylindrical rims; and
   e) rotating said cylindrical rims to continuously transport said elastomeric web from said close spacing at said first location to said far spacing at said second location thereby stretching said elastomeric web in said cross machine direction wherein said rotating is provided by a driving means which is connected to said rims.

2. The method of claim 1 wherein said guiding step includes the step of providing said supporting means which includes at least three support rollers rotatably connected to said inner circumferential surface of said cylindrical rims.

3. The method of claim 1 wherein said holding step includes the step of providing said gripping means which includes a pair of endless belts which receive said elastomeric web and hold said elastomeric web against said outer circumferential surface of said cylindrical rims between said first location and said second location.

4. The method of claim 1 wherein said rotating step includes the step of providing said driving means which includes a pair of drive gears which engage and rotate a pair of ring gears which are connected to said inner circumferential surface of said cylindrical rims thereby rotating said cylindrical rims.

5. The method of claim 1 wherein said rotating step includes the step of providing said driving means which includes a pair of endless belts which engage a portion of said outer circumferential surface of each of said cylindrical rims and rotate said rims.

6. The method of claim 1 wherein said rotating step includes the step of stretching said elastomeric web in said cross machine direction in an amount of from about 20 to about 400 percent.

7. The method of claim 1 wherein said moving step includes the step of providing said elastomeric web which is a polyurethane film.

8. The method of claim 1 further comprising the step of elongating said elastomeric web in said machine direction before said step of holding said elastomeric web.

9. The method of claim 1 wherein said inner circumferential surface of said cylindrical rims defines a diameter of from about 61 to about 381 centimeters.

10. An apparatus for stretching a continuously moving elastomeric web in a cross machine direction, said apparatus comprising:

a) a supplying means for continuously moving said elastomeric web in a machine direction along an elastomeric web path;

b) a pair of rotatable, cylindrical rims which are located adjacent said elastomeric web wherein each of said rims has an axis, an inner circumferential surface, an outer circumferential surface and a center opening therethrough which allows access through said cylindrical rim when in use;

c) a supporting means connected to said inner circumferential surface of said cylindrical rims for guiding said rims for rotation about said axes wherein said axes are oriented to position said rims at a close spacing at a first location and a far spacing at a second location, said far spacing being greater than said close spacing relative to said elastomeric web path;

d) a gripping means located on said cylindrical rims for receiving said elastomeric web and holding said elastomeric web as said elastomeric web is stretched; and e) a driving means connected to said cylindrical rims for rotating said rims, wherein, as said cylindrical rims are rotated by said driving means, said elastomeric web is received by said gripping means at said close spacing at said first location and transported to said far spacing at said second location thereby stretching said elastomeric web in said cross machine direction.

11. The apparatus of claim 10 wherein said supporting means includes at least three support rollers which are rotatably connected to said inner circumferential surface of said cylindrical rims.

12. The apparatus of claim 10 wherein said gripping means includes a pair of endless belts which are configured to receive said elastomeric web and hold said elastomeric web against said outer circumferential surface of said cylindrical rims between said first location and said second location as said rims are rotated.

13. The apparatus of claim 10 wherein said driving means includes a pair of drive gears which are configured to engage and rotate a pair of ring gears which are connected to said inner circumferential surface of said cylindrical rims wherein, in use, said drive gears engage and rotate said ring gears thereby rotating said cylindrical rims.

14. The apparatus of claim 10 wherein said driving means includes a pair of endless belts which are configured to engage a portion of said outer circumferential surface of said cylindrical rims and rotate said rims.

15. The apparatus of claim 14 wherein said gripping means is provided by said endless belts which are further configured to receive said elastomeric web and hold said elastomeric web against said outer circumferential surface of said cylindrical rims between said first location and said second location as said rims are rotated.

16. The apparatus of claim 10 wherein said supporting means further includes an adjusting means for changing an orientation of said axes of said cylindrical rims to vary said close spacing at said first location and said far spacing at said second location relative to said elastomeric web path to provide a variable amount of stretch to said elastomeric web in said cross machine direction.

17. The apparatus of claim 10 wherein said inner circumferential surface of said cylindrical rims defines a diameter of from about 61 to about 381 centimeters.

18. A method for providing a laminated web which is stretchable in a cross machine direction, said method comprising the steps of:

a) moving an elastomeric web in a machine direction along an elastomeric web path;

b) moving at least one facing sheet along a facing sheet path;

c) stretching said elastomeric web in said cross machine direction thereby providing a stretched elastomeric web;

d) positioning said stretched elastomeric web and said facing sheet in a facing relationship; and e) bonding said stretched elastomeric web to said facing sheet thereby providing said laminated web which is stretchable in said cross machine direction, wherein said step of stretching comprises the steps of:

f) providing a pair of rotatable, cylindrical rims adjacent said elastomeric web wherein each of said rims has an axis, an inner circumferential surface, an outer circumferential surface and a center opening therethrough and wherein said facing sheet extends along said facing sheet path through said center opening in at least one of said cylindrical rims before said step of bonding;

g) guiding said cylindrical rims for rotation about said axes wherein said axes are oriented to position said rims at a close spacing at a first location and a far spacing at a second location, said far spacing being greater than said close spacing relative to said elastomeric web path and wherein said guiding is provided by a supporting means which is connected to said cylindrical rims;

h) holding said elastomeric web between said first location and said second location wherein said holding is provided by a gripping means which is located on said cylindrical rims; and i) rotating said cylindrical rims to continuously transport said elastomeric web from said close spacing at said first location to said far spacing at said second location thereby stretching said elastomeric web in said cross machine direction wherein said rotating is provided by a driving means which is connected to said cylindrical rims.

19. The method of claim 18 further including the step of providing a web guiding means located between said cylindrical rims for orientating said facing sheet along said machine direction after said facing sheet extends through said center opening in said cylindrical rim.

20. The method of claim 18 wherein said rotating step includes the step of providing a driving means which includes a pair of drive gears which engage and rotate a pair of ring gears which are connected to said inner circumferential surface of said cylindrical rims thereby rotating said cylindrical rims.

21. The method of claim 18 wherein said rotating step includes the step of stretching said elastomeric web in the cross machine direction in an amount of from about 20 to about 400 percent.

22. The method of claim 18 wherein said step of moving said elastomeric web includes the step of providing said elastomeric web which is a polyurethane film.

23. The method of claim 18 wherein said moving step includes the step of providing said facing sheet which is a nonwoven material.

24. The method of claim 18 wherein said step of bonding is provided ultrasonically.

25. The method of claim 18 further comprising the step of elongating said elastomeric web in said machine direction before said step of bonding said stretched elastomeric web to said facing sheet thereby providing a laminated web which is stretchable in both said machine direction and said cross machine direction.

26. The method of claim 18 further comprising the steps of providing a second facing sheet; and bonding said second facing sheet to said stretched elastomeric web thereby providing said laminated web.

27. The method of claim 18 wherein said inner circumferential surface of said cylindrical rims defines a diameter of from about 61 to about 381 centimeters.

28. An apparatus for stretching a continuously moving elastomeric web in a cross machine direction, said apparatus comprising:

a) a supplying means for continuously moving said elastomeric web in a machine direction along an elastomeric web path;

b) a pair of rotatable, cylindrical rims which are located adjacent said elastomeric web wherein each of said rims defines an axis, an inner circumferential surface, an outer circumferential surface and a center opening therethrough which remains substantially open thereby allowing access through said center opening when in use;

c) a supporting means connected to said cylindrical rims for guiding said rims for rotation about said axes wherein said axes are oriented to position said rims at a close spacing at a first location and a far spacing at a second location, said far spacing being greater than said close spacing relative to said elastomeric web path;

d) a gripping means located on said cylindrical rims for receiving said elastomeric web and holding said elastomeric web as said elastomeric web is stretched; and e) a driving means connected to said cylindrical rims for rotating said rims, wherein said cylindrical rims are not supported or driven about said axes of said cylindrical rims and wherein, as said cylindrical rims are rotated by said driving means, said elastomeric web is received by said gripping means at said close spacing at said first location and transported to said far spacing at said second location thereby stretching said elastomeric web in said cross machine direction.

29. The apparatus of claim 28 wherein said supporting means and said driving means do not extend along said axes of said cylindrical rims.

30. A method for stretching a continuously moving elastomeric web in a cross machine direction, said method comprising the steps of:

a) moving said elastomeric web in a machine direction along an elastomeric web path;

b) providing a pair of rotatable, cylindrical rims adjacent said elastomeric web wherein each of said rims has an axis, an inner circumferential surface, an outer circumferential surface and a center opening therethrough;

c) guiding said cylindrical rims for rotation about said axes wherein said axes are oriented to position said rims at a close spacing at a first location and a far spacing at a second location, said far spacing being substantially greater than said close spacing relative to said elastomeric web path and wherein said guiding is provided by a supporting means which is connected to said cylindrical rims;

d) holding said elastomeric web between said first location and said second location wherein said holding is provided by a gripping means which is located on said cylindrical rims; and e) rotating said cylindrical rims to continuously transport said elastomeric web from said close spacing at said first location to said far spacing at said second location thereby stretching said elastomeric web in said cross machine direction wherein said rotating is provided by a driving means which is connected to said rims and wherein said center opening in each of said cylindrical rims remains substantially open when said cylindrical rim is rotating and wherein said cylindrical rims are not supported or driven about said axes of said cylindrical rims.

31. The method of claim 30 wherein said center opening defines a diameter of from about 61 to about 381 centimeters which remains substantially open when in use.

* * * * *